(12) United States Patent
Tsaur

(10) Patent No.: US 6,395,691 B1
(45) Date of Patent: May 28, 2002

(54) PERSONAL WASH COMPOSITIONS CONTAINING PARTICLE-IN-OIL DISPERSION

(75) Inventor: Liang Sheng Tsaur, Norwood, NJ (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/796,151

(22) Filed: Feb. 28, 2001

(51) Int. Cl.[7] ............................. A61K 7/50; C11D 3/18
(52) U.S. Cl. .................. 510/130; 510/158; 510/159; 510/417; 510/473; 510/474
(58) Field of Search ................ 510/130, 159, 510/473, 474, 417, 158

(56) References Cited

U.S. PATENT DOCUMENTS

| | | | |
|---|---|---|---|
| 5,661,189 A | * | 8/1997 | Grieveson .................. 514/784 |
| 5,804,540 A | | 9/1998 | Tsaur et al. |
| 5,869,070 A | | 2/1999 | Dixon et al. |
| 5,912,002 A | | 6/1999 | Grieveson et al. |
| 6,066,608 A | * | 5/2000 | Glenn, Jr. .................. 510/159 |

OTHER PUBLICATIONS

Copending application: Applicant: Tsaur et al., Serial No.: 09/796,150, Filed: Feb. 28, 2001, For: Process For Making Mild Moisturizing Liquids Containing Large Oil Droplet In–Oil Dispersion.

* cited by examiner

*Primary Examiner*—Necholus Ogden
(74) *Attorney, Agent, or Firm*—Ronald A. Koatz

(57) ABSTRACT

The invention provides personal wash liquids comprising stable particle-in-oil dispersion designed to better deliver functional ingredients from such liquids. Specifically, the invention defines compositions for delivering solid particles and/or capsules.

3 Claims, No Drawings

PERSONAL WASH COMPOSITIONS CONTAINING PARTICLE-IN-OIL DISPERSION

FIELD OF THE INVENTION

The present invention relates to liquid personal wash compositions to effectively deposit solid particles comprising (a) surfactant (synthetic surfactant with or without soap); (b) large particle-in-oil dispersions comprising (i) a solid particle (0.1 to 150 microns, preferably 0.2 to 100 microns) or (ii) a capsule in either petrolatum or in a hydrocarbon oil which is thickened or structured with an oil-mixable polymer; and (c) water soluble thickener mixable with the surfactant (e.g., concentrated surfactant) which can prevent physical separation of the large particle-in-oil dispersions (dispersions having size greater than 50 microns) and are capable of preventing separation of large particle-in-oil dispersions for over 3 months.

BACKGROUND

Deposition of emollient oils from liquid cleansers can be achieved using small droplet deposition assisted with cationic polymer or by using large drops. However, deposition of solid particles (e.g., hydrophilic particle) from a cleansing product (e.g., wash-off cleanser) remains technically challenging.

U.S. Pat. No. 5,661,189 to Grieveson discloses an aqueous liquid and a moisturizing composition containing emollients thickened with a hydrophobic thickener which emollients have a particle in the range of 50–500 $\mu$. These are thickened particles, not particle in oil dispersions.

U.S. Pat. No. 5,804,540 to Tsaur discloses personal wash liquids comprising low viscosity oils pre-thickened by non-antifoaming hydrophobic polymers.

Again, the reference fails to teach or suggest solid cosmetic particles or capsules as particle-in-oil dispersions. Further, there is no disclosure of a particle-in-oil dispersion in a surfactant system comprising water soluble thickener mixable with surfactant.

U.S. Pat. No. 5,869,070 to Dixon et al. discloses stable liquid cleansing compositions with skin moisturizing agent and gel forming polymer. Skin moisturizing agents are petrolatum, polybutene and mixtures of petrolatum/polybutene with ratio of 3:1 to 5:1.

The reference fails to disclose solid, particle (e.g., cosmetic particle) in oil or capsules in oil. Further, although petrolatum/polybutylene is disclosed as moisturizer, there is no teaching or suggestion of a separate oil thickened by petrolatum/polybutylene. Finally, there is no teaching or suggestion of particle-in-oil found in a thickened/concentrated surfactant system.

U.S. Pat. No. 5,912,002 to Grieveson et al. discloses cleansing composition comprising surfactant and internal emulsion comprising cosmetic agent, emulsifier and carrier.

Grieveson differs from the compositions of the invention in that compositions of the subject invention require that the oil (of "particle in oil") is capable of separating and entrapping solid particles in presence of concentrated surfactant solution and without need of emulsifier. By contrast, Grieveson is an oil-in-oil emulsion where stability is achieved only by using an emulsion. Further, the oil (carrier oil) of Grieveson can be any oil in the range of 200 to 500,000 centistokes at 25° C while, in the subject invention, oil viscosity must be higher than 10,000 centistokes at 0.1 $S^{-1}$.

BRIEF SUMMARY OF THE INVENTION

Unexpectedly, applicants have now found a superior way to deliver (a) solid particles; and/or (b) capsule (e.g., perfume-containing capsules) from a wash-off liquid by forming a particle-in-oil dispersion; wherein particle refers to any of (a) or (b) above; wherein the oil is petrolatum; or emollient oils which contain an oil mixable polymer; and wherein the surfactant system in which the particle-in-oil dispersion is found is thickened/concentrated (e.g., with xanthan gum or other thickener). The particle-in-oil dispersion remains stable at room temperature for greater than 3 months with no visible physical separation and, in use, deposits far greater amounts of solid particle/capsule from a wash-off liquid composition than would be possible if the particles were added alone rather than as particle-in-oil dispersion.

More specifically, the invention comprises:

A personal liquid composition comprising:

(1) 5% to 30%, preferably 8% to 25% by wt. of a surfactant selected from the group consisting of anionic surfactants, amphoteric surfactants, nonionic surfactants, cationic surfactants and mixtures thereof;

(2) 0.5% to 5% by wt. of a water soluble thickener mixable with said surfactant(s) and which prevents physical separation of a particle-in-oil dispersion as noted in (3) below from the liquid cleanser for three months or more as measured at room temperature; and (3) 2% to 20% by wt. of said particle-in-oil dispersion comprising:

(a) 60% to 99% by wt. of said dispersion of petrolatum; or hydrocarbon oil containing oil mixable polymer, wherein said petrolatum or polymer containing oil can suspend solid particles having density greater than 1.05 (without need of an emulsifier, although such emulsifier may be optionally added if desired);

(b) 1% to 40% by wt. of a "particle" selected from the group consisting of (i) solid particles with particle size in range 0.1 to 250, preferably 0.2 to 100 microns; and (ii) capsules with size in the range of 1–200 microns, wherein the particle-in-oil dispersion is itself stable at room temperature for over 3 months;

wherein the particle-in oil dispersion has size of about 50 to 5000 microns, preferably 100–1000 microns; and wherein particle-in-oil dispersion is stable in the composition for three months or more at R.T.

DETAILED DESCRIPTION OF THE INVENTION

The present invention relates to compositions for delivering solid particles (preferably hydrophilic solid particles) and/or capsules (e.g., perfume-containing capsules) from wash off liquid compositions. These "particles" (referring generally to the solid particles, and capsules) are delivered from relatively large size (50 to 5000 microns), stable (for at least three months at room temperature), particle-in-oil dispersions found in thickened/concentrated surfactant compositions wherein the entire composition (containing particle-in-oil dispersion) is itself stable for three months at room temperature.

The compositions, as described below, will be defined by (a) surfactant system; (2) thickening system for said surfactant system; and (3) particle-in-oil composition wherein the particle-in-oil composition is itself defined by (a) particles (e.g., solid particle or capsules) and (b) oil in which particles are found. The oil is petrolatum; or oil containing oil-mixable polymers to help further suspend/stabilize particles.

The invention is thus defined in more detail below.

SURFACTANT SYSTEM

The composition of the invention comprises 5 to 30% by wt. surfactant. The surfactants in the composition may be anionic, nonionic, amphoteric/zwitterionic, cationic or mixtures thereof.

The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGES); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium laurel ether sulfates are preferred.

These differ from ether sulfates of the invention in that they are not branched.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$–$C_{22}$ alkyl and M is a solubilizing cation; amido-MIPA sulfosuccinates of formula $$RCONH(CH_2)CH(CH_3)(SO_3M)CO_2M$$

where M is as defined above.

Also included are the alkoxylated citrate sulfosuccinates; and alkoxylated sulfosuccinates such as the following:

$$R\text{—}O\text{—}(CH_2CH_2O)_n\overset{O}{\overset{\|}{C}}CH_2CH(SO_3M)CO_2M$$

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula $$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$$R\text{-}(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application. This compound has the general formula:

In general the anionic component will comprise from about 1 to 20% by weight of the composition, preferably 2 to 15%, most preferably 5 to 12% by weight of the composition. It may also include a C8 to C14 unbranched fatty acid hydrocarbon (e.g., lauric acid, palmitic acid, capric, etc.).

ZWITTERIONIC AND AMPHOTERIC SURFACTANTS

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$R^2\text{—}\overset{\overset{\displaystyle (R^3)_x}{\displaystyle |}}{Y^{(+)}}\text{-}CH_2\text{—}R^4Z^{(-)}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of for example nitrogen, atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

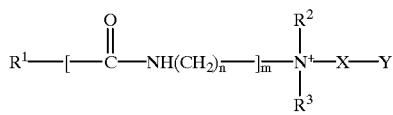

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —$CO_2$— or —$SO_3$—

Suitable amphoteric detergents within the above general formula include simple betaines of formula:

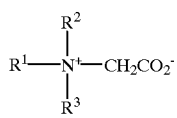

and amido betaines of formula:

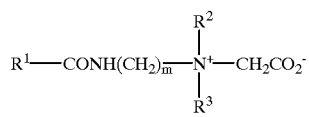

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

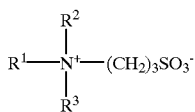

or

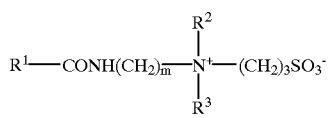

where m is 2 or 3, or variants of these in which —$(CH_2)_3SO$—$_3$ is replaced by

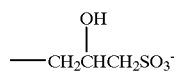

In these formulae $R^1$, $R^2$ and $R^3$ are as discussed previously.

Amphoacetates and diamphoacetates are also intended to be covered in possible zwitterionic and/or amphoteric compounds which may be used.

The surfactant system may also optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula

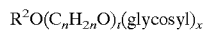

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Nonionic generally comprises 0 to 10% by wt. of the composition.

Cationic synthetic surfactant should not serve as the sole surfactant in this product, but cam be used as a co-surfactant at a lower level of from about 0.5% to about 6% by weight. The more preferred types of cationic surfactant are selected from the group consisting of: alkyl trimonnium chloride and methosulfate, and dialkyldimonnium chloride and methyl sulphate, and alkyl alkonium chloride and methyl sulphate and mixtures thereof. These surfactants contain $C_{12}$ to $C_{24}$ carbon atoms per alkyl chain. The most preferred cationic is selected from the group consisting of stearalkonium chloride, stearyltrimonium chloride. Di-stearyl-dimonium chloride, and mixtures thereof.

THICKENING SYSTEM

Another required component of the invention is organic, inorganic or polymeric stabilizer. Specifically, the compositions comprise 0.1 to 10% by wt. of an organic, inorganic or polymeric stabilizer which provides physical stability of the large oil droplets, (droplets of polymer/oil blend) in the surfactant composition at 40° C. for over four weeks.

Generally the organic polymeric stabilizer of the invention include, but are not limited to any of several long chain acyl derivatives or mixtures thereof. Included are the glycol mono- di- and triesters having about 14 to about 22 carbon atoms. Preferred glycol esters include the ethylene glycol mono- and distearates, glyceryl stearates, palm oil glyceride, tripalmitin, tristearin and mixtures thereof. Another example of suspending agent useful in the present invention include the alkanolamides having from about 14 to about 22 carbon atoms. Preferred alkanolamides are stearic monoethanolamide, stearic diethanolamide stearic monoisopropanolamide, stearic monoethanolamide stearate and mixtures thereof. Still another example of a suspending agent useful in the present invention include the long chain fatty acid esters such as stearyl stearate, stearyl palmitate, palmityl palmitate, trihydroxystearylglycerol and tristearylglycerol. Still another example of a suitable suspending agent useful in the present invention include the long chain amine oxides having from about 14 to about 22 carbon atoms. Preferred amine oxides are hexadecyldimethylamine oxide and octadecyldimethylamide oxide.

Example of a suitable polymeric suspending agent (or thickening agent) useful in the present invention include the carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, hydroxymethyl carboxypropyl cellulose, methyl cellulose, ethyl cellulose, guar gum, gum karaya, gum tragacanth, gum arabic, gum acacia, gum agar, xanthan gum and mixtures thereof. Preferred carbohydrate gums are the cellulose gums and xanthan gum. Of all the above described types of suspending agents, preferred compounds include the long chain glycol ester and the carbohydrate gums. Other stabilizers which may be used are set forth in U.S. Pat. No. 5,854,293 to Glenn, Jr. at column 4, line 36 to column 6, line 65. This reference is hereby incorporated by reference into the subject application.

The thickener may also be a cationic polymer. Suitable cationic polymers include Guar hydroxypropyltrimonium chloride, Quaternium-19, -23, -40, -57, poly (dimethyidiallylammonium chloride), poly (dimethyl butenyl ammonium chloride)-, w-bis (triethanolammonium chloride), poly (dipropyidiallylammonium chloride), poly (methyl-beta propaniodiallylammonium chloride), poly (diallylpiperidinium chloride), poly (vinyl pyridinium chloride), quaternised poly (vinyl alcohol), quaternized poly (dimethylaminoethylmethacrylate) and mixtures thereof.

The suspending agent or mixtures of agent may be present from about 0.1 to 10% of the composition.

While not wishing to be bound by theory, thickener is delivered to aid in suspension of the particle-in-oil dispersion.

Specifically, the thickened surfactant system prevents physical separation of particle-in-oil dispersion for over three months.

PARTICLE-IN-OIL DISPERSION

The particle-in-oil dispersion comprises solid particles and well-structured oil that can stably suspend and entrap the solid particles in a concentrated surfactant solution. Stability of the particle-in-oil dispersion is achieved by the viscosity and the suspension power of the oil.

The suspended solid particles can be either inorganic or organic particles. Examples of inorganic include but are not limited to silica, talc, mica; and examples organic particles are silicone powders or capsules such as perfume capsules or vitamin E capsules. Capsules suitable for this invention are free flow powders prepared by various encapsulation processes such as interfacial polymerization encapsulation, coacervation encapsulation, spray drying/cooling encapsulation or spray coating encapsulation. These solid particles should be cosmetic grade approved for personal cleansing application. Typically the solid particles will have particle size of 0.1 to 150 microns, preferably 0.2 to 100 microns.

The well-structured oil is defined as emollient oil that has a viscosity higher than 10,000 cps at $0.1\ S^{-1}$ and can stably suspend the solid particles at room temperature for over 3 months without visible physical separation. Preferably well-structured oil is petrolatum or emollient oil structured/thickened with oil mixable polymers. Examples of emollient oils are mineral oils, triglycerides oils such as sunflower seed oil, castor oil or soybean oil, alkyl esters such as isopropylpalmitate or isopropylmyristate and silicone oils. These emollient oils alone are not useful for the invention due to its poor suspension/entrapping properties. To suspend and entrap dense solid particles, oil mixable polymer is required to add into these emollient oils. The oil mixable polymer works as a thickener and also works as structuring agent to suspend the solid particles. Examples of possible oil mixable polymers are hydrogenated or non-hydrogenated polymer of alkylene or isoalkylene such as polybutene, poly-alphaolefin, or polyester, polyacrylate and it's copolymer, and rubber thermoplastic block copolymers such as butadiene/styrene or styrene/butylene di- or tri-block copolymers. Most preferably oil mixable polymers are rubber based thermoplastic block polymers available from Shell Chemical Company under the tradename of Kraton®.

In general, the oil drop should be 5 times or greater (i.e., at least 5 times as great) as the size of the suspended particles.

Typically the well structured oil comprises 60% to 99%, preferably 70% to 95% of the particle-in-oil dispersion and the solid particle comprises 1% to 40%, preferably 5% to 30% of the dispersion.

OTHER INGREDIENTS

In addition to ingredients noted above, the composition (i.e., surfactant composition) may comprise any one of various ingredients which may be found in personal wash compositions, including organic solvents (e.g., polyols such as $C_1$ to $C_4$ alkanols), auxiliary thickeners, sequestering agents (e.g., tetrasodium ethylenediaminetetraacetate), coloring agents, opacifiers, and pearlizers.

The compositions may also include antimicrobial agents, alkanolamides, antioxidants (e.g., butylated hydroxytoluene), exfoliants (polyoxyethylene beads) etc.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLE 1

DEPOSITION OF SOLID PARTICLES

The following example shows how deposition of large solid particles from liquid cleanser can be dramatically enhanced using stable particle-in-oil dispersions of this invention. The "particles" used for these examples were two glitters—visible Spectratek Geometic Silver Pigments of 100×100 micron s and 100×50 microns.

First, applicants prepared a liquid cleansing base with composition as noted below in Table 1 for incorporation of the stable glitter-in-oil dispersions:

TABLE 1

Composition of Liquid Cleansing Base

| | |
|---|---|
| Lauric Acid | 2.88 wt. % |
| Triethanol Amine | 2.0 wt. % |
| Na Lauroamphoacetate | 5.8 wt. % |
| Na Lauryl Sulfosuccinate | 5.8 wt. % |
| Xanthan Gum | 1.2 wt. % |
| Glycerin | 10.0 wt. % |
| DMDM HYDANTOIN | 0.20 wt. % |
| Perfume | 0.5 wt. % |
| Water | To 100 wt. % |

It should be noted that the liquid base is a thickened base, i.e., thickened with xanthan gum.

Applicants next prepared glitter-in-oil dispersions noted below in Table 2:

TABLE 2

Composition of Glitter-in-Oil Dispersion

Particle-in-Oil Composition

| | |
|---|---|
| Example 1A | 10% Spectratek 100 × 100 microns Geometric Silver (e.g., "particle") |
| | 90% petrolatum/polybutene (Panalane H300E) 2 to 1 ratio (e.g., oil and oil soluble polymer) |
| Example 1B | 10% Spectratek 100 × 50 microns Geometric Silver |
| | 90% petrolatum/polybutene (Panalane H300E) 2 to 1 ratio |

Example 1A and 1B were prepared by first injecting 8 parts of the prepared glitter-in-oil dispersion shown in Table 2 into 92 parts of xanthan-thickened liquid cleanser using a syringe pump to form big noodle-like particles. The mixture was then passed through a screen with 500 micron openings once to make glitter-in-oil dispersions with particle size larger than 300 microns. Examined under microscope, these glitters are well entrapped inside the petrolatum/polymer oil droplet for both examples.

Two comparative examples were also prepared for comparison. Comparative Example 1 was prepared by mixing 0.8 parts. of glitter, Spectratek 100×100 Geometric Silver pigment, with 99.2 parts xanthan-thickened liquid base at room temperature (i.e., it was not glitter-in-oil dispersion, only glitter in general composition). Comparative Example 2 was prepared by first injecting 7 parts of petrolatum/Panalene H300 (2/1 ratio) into 93 parts Comparative Example 1. The cleanser was then passed through a screen with 500 micron opening once to make the Comparative Example 2. In Comparative 2, the oil and glitter were separate dispersions in the liquid.

Arm washed with either Example 1A or 1B showed much higher amount of visible shining particles retained on the skin than the arm washed with either Comparative Example 1 or Comparative Example 2. This example has clearly showed that deposition of solid particles from a liquid personal washing product can be achieved using stable particle-in-oil dispersion as claimed in the invention. To achieve such deposition, the solid particle should be stably entrapped inside the oil droplet.

EXAMPLE 2

Four examples were prepared to show the effect of oil suspension properties on stability of particle-in-oil dispersion in a liquid cleanser as noted below:

TABLE 3

Composition of Particle-in-Oil Dispersion

| | |
|---|---|
| Example 2A | 5% Timiron MP 1005, less than 15 microns mica from Rona |
| | 95% petrolatum |
| Example 2B | 5% Timiron MP 1005, less than 15 microns mica from Rona |
| | 95% Geahlene 500 from Penreco (mineral oil thickened with oil mixable polymer) |
| Comparative 1 | 5% Timiron MP 1005, less than 15 microns mica from Rona |
| | 95% mineral oil |
| Comparative 2 | 5% Timiron MP 1005, less than 15 microns mica from Rona |
| | 95% DC 200, 5,000 cps silicone oil |

Two of the oils, petrolatum and Geahlene 500 (which is mineral oil thickened with a block copolymer), have good suspension properties suitable for the invention. The other two oils, mineral oil and silicone oil, do not have good suspension properties to stably suspend large particles in the oil and are not suitable for the application of this invention. The particle-in-oil dispersion was prepared by mixing 5 parts Timiron with 95 parts oil at 50° C. for 10 to 20 minutes and cooled to room temperature before added into a liquid cleanser. The prepared particle-in-oil dispersions are stable at room temperature to both petrolatum and Geahlene 500 for over 3 months, but not stable for either silicone oil or mineral oil.

5 parts of the above prepared particle-in-oil dispersion was then added into 95 parts liquid cleansing base using the xanthan structured liquid and the method described in Example 1. Mica was retained well inside the oil phase for Example 2A and 2B. For the comparative examples, most of the micas were released into the cleanser. These examples show that oil suspension properties is very critical in the invention so that liquid cleansers containing particle-in-oil dispersion may deposit the entrapped particles on skin surface for improved sensory or skin care properties. To be useful for the application, the particle-in-oil dispersion should be stable at room temperature for at least 3 months without visible physical separation.

EXAMPLES 3–6

In order to show that solid grade particles (not just glitter) could be used, applicants prepared (i) micron size talc, (ii) mica (iii) $TiO_2$, and (iv) silicone powder as particles. Talc, mica, and silicone powder (micron size) are used to manipulate tactile properties; and $TiO_2$ (in form of submicron, water-dispersible $TiO_2$) is for UV protection. Compositions of the dispersion are set forth in. Table 4 below:

TABLE 4

Composition of Particle-in-Oil Dispersion

| | |
|---|---|
| Example 3 | 30% Cimpact 710, 1.6 microns talc from Luznac America (particle)<br>70% petrolatum (oil) |
| Example 4 | 10% Timiron MP 1005, less than 15 microns mica from Rona (particle)<br>90% petrolatum (oil) |
| Example 5 | 10% Titan M212, submicron water-dispersible $TiO_2$ ex. Preserpse Inc. (particle)<br>90% petrolatum (oil) |
| Example 6 | 10% 9506 silicone powder from Dow Corning (particle)<br>90% petrolatum/polybutene H300E of 2 to 1 ratio (oil) |

All the above particle-in-oil dispersions are stable at R.T. for 3 months. Examples 3–6 were prepared by adding 8 parts of the oil dispersion into 92 parts of the xanthan-structured liquid using the method and base of Example 1.

This example shows dry skin, after wash skin feel can be manipulated by using various particles. Particles as noted were stable in liquid for over 3 months.

EXAMPLE 7

Perfume Capsules-in-Oil

Liquid compositions with perfume-in-oil dispersion are set forth in Table 5 below:

TABLE 5

Liquid Composition Containing Perfume Capsule-in-Oil Dispersion

| | |
|---|---|
| Example 5A | 92 parts: xanthan-thickened liquid<br>8 parts: 15% 180 micrometers Limonene Capsule (ex. 3M) (particle) dispersed in 85% petrolatum (oil) |
| Example 5B | 92 parts xanthan-thickened liquid<br>8 parts: 30 micrometers Limonene Capsule (ex 3M) (particle) dispersed in 85% petrolatum (oil) |

Same procedure described in Example 1 was used to prepare Examples 5A and 5B with composition shown in Table 4. A xanthan-thickened liquid with the composition same as that shown in Table 1 without perfume was prepared for the incorporation of perfume capsule-in-oil dispersion. A control sample prepared by mixing 1 part of free limonene fragrance with 99 parts of xanthan-thickened liquid at room temperature was used for comparison. Sample 5A showed much better perfume retention than the comparative example. Arms washed with Sample 5A have much stronger fresh limolene smell than the comparative example containing free limonene fragrance.

What is claimed is:

1. A personal liquid composition comprising:
   (a) a surfactant system comprising:
      (i) 5% to 30% by wt. of surfactant selected from the group consisting of anionic surfactant, amphoteric surfactant, nonionic surfactant, cationic surfactant and mixtures thereof; and
      (ii) 0.1% to 10% by wt. water soluble thickener within said surfactant system;
   (b) 2% to 20% by wt. of a particle-in-oil dispersion comprising:
      (i) 60 to 99% by wt. of petrolatum or thickened emollient oil which contains oil mixable polymers, which petrolatum or thickened oil have a viscosity higher than 10,000 cps when measured at 1 $S^{-1}$ and can suspend solids having a density greater than 1.05 at room temperature over 3 months, without visible physical separation; and
      (ii) 1 to 40% by wt. of a particle selected from the group consisting of:
         (a) solids having a particle size of 0.5 to 150 microns; and
         (b) capsules in size range of 1 to 200 microns;
   wherein the personal liquid composition is prepared by first mixing the particle of item (b)(ii) with the petrolatum or thickened oil of (b)(i) to form particle-in-oil dispersion (b) and subsequently adding said particle-in-oil dispersion (b) into surfactant system (a) to form a particle-in-oil in surfactant solution dispersion having a drop size of 50 to 5000 microns;
   wherein the size of the particle-in-oil drop is at least 5 times larger than the suspended particles; and
   wherein said personal liquid composition is stable over 3 months at room temperature.

2. A composition according to claim 1, wherein thickener oil (a)(ii) is a xanthan gum.

3. A composition according to claim 1, wherein oil (b)(i) is a hydrocarbon oil containing an oil miscible polymer.

* * * * *